(12) United States Patent
Koseoglu

(10) Patent No.: US 12,331,253 B2
(45) Date of Patent: Jun. 17, 2025

(54) INTEGRATED HYDROCRACKING AND CARBON DIOXIDE HYDROGENATION TO PRODUCE OXYGENATED AND HYDROCARBON FUELS

(71) Applicant: Saudi Arabian Oil Company, Dhahran (SA)

(72) Inventor: Omer Refa Koseoglu, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 636 days.

(21) Appl. No.: 17/672,861

(22) Filed: Feb. 16, 2022

(65) Prior Publication Data
US 2023/0257665 A1 Aug. 17, 2023

(51) Int. Cl.
| | | |
|---|---|---|
| C10G 45/00 | (2006.01) | |
| B01J 19/24 | (2006.01) | |
| C01B 3/24 | (2006.01) | |
| C07C 29/151 | (2006.01) | |

(52) U.S. Cl.
CPC ............ *C10G 45/00* (2013.01); *B01J 19/245* (2013.01); *C01B 3/24* (2013.01); *C07C 29/1518* (2013.01); *B01J 2219/0004* (2013.01); *C01B 2203/061* (2013.01); *C01B 2203/065* (2013.01); *C10G 2300/1003* (2013.01)

(58) Field of Classification Search
CPC ... C07C 29/151; C07C 29/1518; C10G 45/00; C10G 2300/1003; C10G 3/50; B01J 19/245; B01J 2219/0004; C01B 3/24; C01B 2203/061; C01B 2203/065; C01B 2203/0233; C01B 2203/062; C01B 3/34; C01B 2203/0811
See application file for complete search history.

(56) References Cited

U.S. PATENT DOCUMENTS

| | | | |
|---|---|---|---|
| 4,219,492 A * | 8/1980 | Konoki | C01B 3/38 252/373 |
| 2009/0313886 A1 | 12/2009 | Hinman et al. | |
| 2010/0143980 A1 | 6/2010 | Balagurunathan et al. | |
| 2011/0158370 A1 | 6/2011 | Morgan | |
| 2012/0245236 A1 | 9/2012 | Suib et al. | |
| 2013/0236809 A1 | 9/2013 | Haan | |
| 2013/0289306 A1 | 10/2013 | Leitner et al. | |
| 2014/0299817 A1 | 10/2014 | Hull et al. | |
| 2015/0133293 A1 | 5/2015 | Khodadadi et al. | |
| 2015/0210621 A1 | 7/2015 | Leitner et al. | |
| 2016/0039724 A1 | 2/2016 | Naterer et al. | |

(Continued)

FOREIGN PATENT DOCUMENTS

| | | | | |
|---|---|---|---|---|
| WO | WO-2010143980 A1 * | 12/2010 | ............... | C01B 3/38 |

*Primary Examiner* — Daniel C. McCracken
*Assistant Examiner* — Joshua Maxwell Speer
(74) *Attorney, Agent, or Firm* — DINSMORE & SHOHL LLP

(57) ABSTRACT

In accordance with one or more embodiments of the present disclosure, a process for producing methanol and hydrocarbon products comprises: generating hydrogen gas and carbon dioxide in a hydrogen production unit; hydroprocessing a hydrocarbon feedstock stream using the hydrogen gas, thereby producing hydrocarbon products and waste hydrogen gas; and contacting the waste hydrogen gas with the carbon dioxide in a hydrogenation unit, thereby producing methanol and product hydrogen gas.

10 Claims, 2 Drawing Sheets

(56) References Cited

U.S. PATENT DOCUMENTS

| | | |
|---|---|---|
| 2016/0067689 A1 | 3/2016 | Peterson et al. |
| 2016/0121306 A1 | 5/2016 | Yu et al. |
| 2016/0280618 A1 | 9/2016 | Mamedov et al. |
| 2018/0015444 A1 | 1/2018 | Porosoff et al. |
| 2018/0221841 A1 | 8/2018 | Tremel |
| 2018/0273454 A1 | 9/2018 | Almusaiteer et al. |
| 2019/0169506 A1 | 6/2019 | Fan et al. |
| 2019/0329227 A1 | 10/2019 | Porosoff et al. |
| 2020/0048173 A1 | 2/2020 | Curulla-Ferre et al. |
| 2020/0222874 A1 | 7/2020 | Manenti |
| 2020/0291901 A1 | 9/2020 | Song |
| 2021/0061656 A1 | 3/2021 | O'Neal et al. |
| 2021/0146344 A1 | 5/2021 | Hwang et al. |
| 2021/0163707 A1 | 6/2021 | Mirkin et al. |
| 2021/0163827 A1 | 6/2021 | Basset et al. |
| 2021/0172682 A1 | 6/2021 | Schuetzle et al. |
| 2021/0322957 A1 | 10/2021 | Stewart et al. |
| 2021/0340077 A1 | 11/2021 | Schuetzle et al. |
| 2021/0354114 A1 | 11/2021 | Stewart et al. |
| 2021/0371362 A1* | 12/2021 | Early .................. C07C 29/74 |
| 2022/0059261 A1 | 2/2022 | Lacroix et al. |
| 2022/0111361 A1 | 4/2022 | Natesakhawat et al. |

\* cited by examiner

INTEGRATED HYDROCRACKING AND CARBON DIOXIDE HYDROGENATION TO PRODUCE OXYGENATED AND HYDROCARBON FUELS

FIELD

Embodiments of the present disclosure generally relate to refining and upgrading hydrocarbon oil, and pertain particularly to a process for producing methanol and other hydrocarbon products from refinery waste products.

TECHNICAL BACKGROUND

Hydrotreating and hydrocracking process technologies (together, often referred to as "hydroprocessing") are used in many petroleum refineries. Hydrotreating a crude oil feed removes unwanted impurities such as sulfur and nitrogen using hydrogen in the presence of a catalyst, thereby producing acceptable transportation fuels or preparing the feedstock for other refining processes. Hydrocracking is a process to refine and convert heavy oil fractions into lighter molecules, which have higher average volatility and higher economic value, using hydrogen at elevated partial pressures in the presence of cracking catalysts. Often, hydrocracking is carried out in two steps: (1) pretreatment and (2) cracking. Heteroatoms, including sulfur, nitrogen, and metals such as Ni and V, are removed in the pretreatment steps to obtain nearly sulfur-free and nitrogen-free effluent. The treated oil is then cracked over a cracking catalyst to obtain final products that can be used in transportation fuels. The products from a hydrocracking unit include naphtha, kerosene, diesel, and unconverted oil. Notably, hydrotreating and hydrocracking both require hydrogen gas as a reagent but also expel excess hydrogen as a waste stream.

Another process requiring hydrogen gas that may be associated with petroleum refining is hydrogenation of carbon dioxide ($CO_2$) to produce methanol. $CO_2$ is a significant contributor to global climate change and should be treated at the site of emission to minimize its escape into the atmosphere. Methanol may be used as a starting material in the production of many higher value products or may even be used as a fuel source.

SUMMARY

Traditionally, waste hydrogen from refining processes could not be used for the hydrogenation of $CO_2$ to methanol because waste hydrogen is not typically produced in refining processes at a significant partial pressure to be separated from other waste gases in an economically feasible manner. Therefore, there is a continual need for systems and processes for using waste hydrogen from refinery operations to produce value added products and consume $CO_2$ to prevent its emission into the atmosphere. Described herein are processes and systems that allow for the production of methanol and hydrocarbon products from refinery waste products, including waste hydrogen.

According to an embodiment, a process for producing methanol and hydrocarbon products is provided. The process comprises: generating hydrogen gas and carbon dioxide in a hydrogen production unit; hydroprocessing a hydrocarbon feedstock stream using the hydrogen gas, thereby producing hydrocarbon products and waste hydrogen gas; and contacting the waste hydrogen gas with the carbon dioxide in a hydrogenation unit, thereby producing methanol and product hydrogen gas.

According to another embodiment, an integrated system for producing methanol and hydrocarbon products using hydrogen gas and carbon dioxide is provided. The system comprises: at least one source of the hydrogen gas; at least one source of the carbon dioxide; and at least one hydrogenation unit in fluid communication with the at least one source of the carbon dioxide and the at least one source of the hydrogen gas.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which.

DETAILED DESCRIPTION

As used herein, the term "hydrocarbon oil" or "hydrocarbon feedstock" refers to an oily liquid composed mostly of a mixture of hydrocarbon compounds. Hydrocarbon oil may include refined oil obtained from crude oil, synthetic crude oil, bitumen, oil sand, shale oil, or coal oil. The term "refined oil" includes, but is not limited to, straight run, hydrotreated, or upgraded vacuum gas oil (VGO), deasphalted oil (DAO) obtained from a solvent deasphalting process, demetallized oil (DMO), light and/or heavy coker gas oil obtained from a coker process, cycle oil obtained from a fluid catalytic cracking (FCC) process, and gas oil obtained from a visbreaking process.

As used herein, the term "hydrocarbon" refers to a chemical compound composed entirely of carbon and hydrogen atoms. An expression such as "$C_x$-$C_y$ hydrocarbon" refers to a hydrocarbon having from x to y carbon atoms. For instance, a $C_1$-$C_5$ hydrocarbon includes methane, ethane, propane, the butanes, and the pentanes.

As used herein, the term "gas hourly space velocity" or "GHSV" refers to the ratio of the gas flow rate of the, for example, hydrogen gas feed to the catalyst volume or mass. Likewise, the term "liquid hourly space velocity" or "LHSV" refers to the ratio of the liquid flow rate of the reagent feed to the catalyst volume or mass.

As used herein, the term "conduit" includes casings, liners, pipes, tubes, coiled tubing, and mechanical structures with interior voids.

As used herein, the term "decreased content" of a substance means that a concentration of the substance is greater before passing through a stage of the process under examination than it is after passing through the stage. As used herein, the term "increased content" of a substance means that a concentration of the substance is greater after passing through a stage of the process under examination than it is before passing through the stage.

As used herein, any stream that is referred to as "rich" in some chemical species contains 50% or more by volume of that chemical species.

In accordance with one or more embodiments, the present application discloses processes and systems that allow for the production of methanol and hydrocarbon products from refinery waste products, including waste hydrogen and CO$_2$. Such waste hydrogen is a low-pressure hydrogen stream for which, until now, there was no practical use. As such, this low pressure hydrogen stream was previously treated as waste and disposed of by flaring. These processes and systems will now be described in greater detail.

Figure 1:
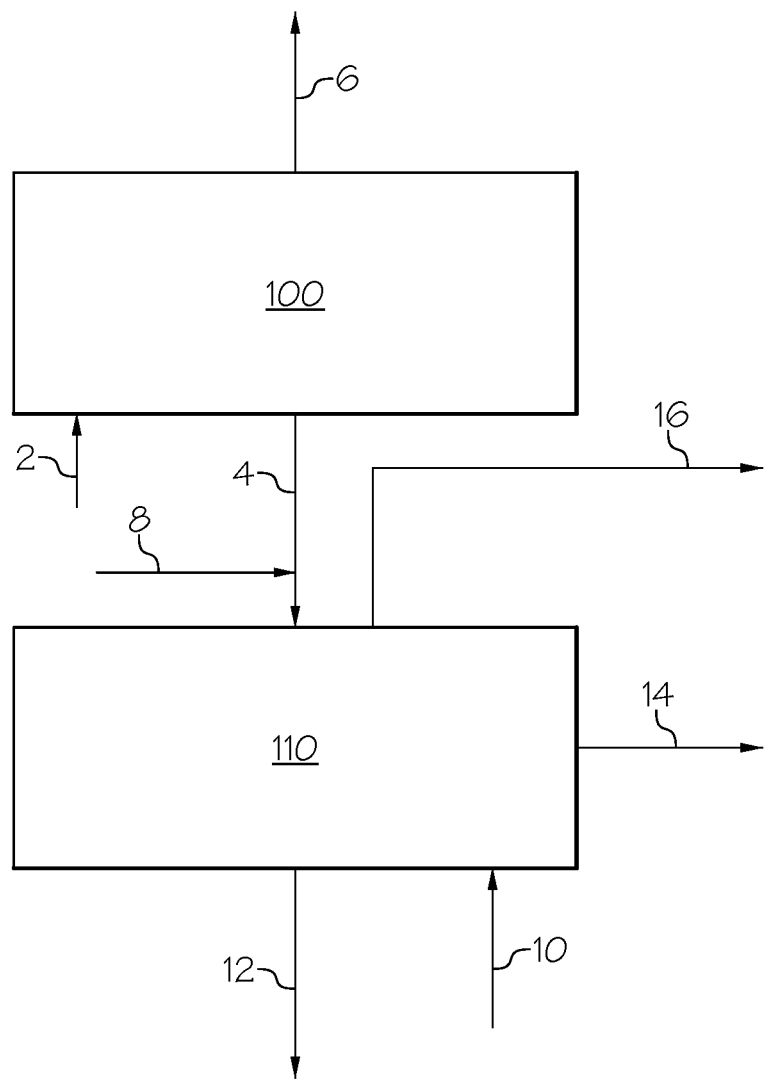
FIG. 1 is a process flow diagram for an exemplary process in accordance with embodiments described herein.

In embodiments, hydrogen gas and CO$_2$ are produced in a hydrogen production unit. FIG. 1 provides a process flow diagram of an embodiment of a hydrogen production unit 100 used to supply hydrogen gas to a hydroprocessor 110. In operation, a hydrocarbon feedstock stream 2 is fed to the hydrogen production unit 100. The hydrocarbon feedstock may be, for example, natural gas comprising methane as a major constituent, along with ethane, propane, butanes, and hydrocarbons having 5 or more carbon atoms as minor constituents. Within the hydrogen production unit 100, the hydrocarbon feedstock is used to produce hydrogen and CO$_2$, which can be separated into a hydrogen gas feed 4 and a CO$_2$ stream 6. The reactions taking place within the hydrogen production unit 100 are depicted as formulae (1) and (2), below. In a first step, the hydrocarbon (such as methane) is reacted with water at high temperature, thereby producing carbon monoxide and hydrogen. In the second step, the carbon monoxide and water react with one another to produce carbon dioxide and hydrogen. In this regard, "high temperature" refers to a temperature from 700° C. to 1000° C. Typical pressures may be from 0.3 MPa to 2.5 MPa.

$$CH_4 + H_2O \rightarrow CO + 3H_2 \quad (1)$$

$$CO + H_2O \rightarrow CO_2 + H_2 \quad (2)$$

The resulting hydrogen gas feed 4 may be fed to the hydroprocessor 110 along with the hydroprocessing feedstock stream 8. The hydroprocessing feedstock stream 8 may be one or more of crude oil or its fractions, such as naphtha, kerosene, diesel, vacuum gas oil, or vacuum residue, for example. The hydroprocessing feedstock stream 8 may include hydrocarbons (including, but not limited to, hydrocarbons boiling in the naphtha range (from 36° C. to 180° C.) and the diesel range (from 180° C. to 370° C.), and heavy molecules (including, but not limited to, vacuum gas oil (boiling from 370° C. to 565° C.) and vacuum residue (boiling at 565° C. and higher). In addition, water stream 10 may be added to the hydroprocessor 110 downstream of the reactor to prevent ammonium sulfide salt precipitation. Within the hydroprocessor 110, the hydrocarbons of the hydroprocessing feedstock stream 8 may be refined, and the heavy molecules may be cracked into light molecules of high economic value. Such light molecules include, but are not limited to naphtha and diesel.

In embodiments, the hydroprocessor 110 may include a hydrotreating unit, a hydrocracking unit, a residue hydrocracking unit, or a combination of two or more of these reactor types. Reactor conditions, such as temperature, pressure and LHSV, are determined by the feedstock being processed as well as the stage of the hydroprocessing.

For instance, when naphtha and/or kerosene are/is hydrotreated, the reactor temperature may be from 330° C. to 370° C., the hydrogen partial pressure may be from 1 MPa to 2 MPa, and the LHSV may be from 4 h$^{-1}$ to 6 h$^{-1}$. When gas oil is hydrotreated, the reactor temperature may be from 340° C. to 400° C., the hydrogen partial pressure may be from 2 MPa to 6 MPa, and the LHSV may be from 1 h$^{-1}$ to 4 h$^{-1}$. When vacuum gas oil is hydrotreated, the reactor temperature may be from 360° C. to 400° C., the hydrogen partial pressure may be from 4 MPa to 8 MPa, and the LHSV may be from 0.5 h$^{-1}$ to 2 h$^{-1}$. Exemplary hydroprocessing catalysts include supported metal catalysts. For instance, such a catalyst may be one or both of cobalt-molybdenum on alumina and/or nickel-molybdenum on alumina. Of course, other metals, such as indium, and other supports are envisioned.

When using a hydrocracking unit, typical hydrocarbon feedstocks include vacuum gas oil, deasphalted oil, and FCC cycle oils. The reactor temperature may be from 350° C. to 450° C., the hydrogen partial pressure may be from 10 MPa to 20 MPa, and the LHSV may be from 0.3 h$^{-1}$ to 2 h$^{-1}$. Exemplary hydrocracking catalysts include supported metal catalysts. Exemplary active metals include nickel-tungsten, and nickel-molybdenum. Exemplary supports include alumina, silica-alumina, and zeolite supports. Of course, other metals and supports are envisioned.

When using a residue hydroprocessing unit, typical feedstocks include atmospheric residue and vacuum residue. The reactor temperature may be from 380° C. to 450° C., the hydrogen partial pressure may be from 15 MPa to 22 MPa, and the LHSV may be from 0.2 h$^{-1}$ to 0.5 h$^{-1}$. Exemplary hydrocracking catalysts include supported metal catalysts. Exemplary active metals include nickel-tungsten, and nickel-molybdenum. Exemplary supports include alumina, silica-alumina, and zeolite supports. Of course, other metals and supports are envisioned.

In embodiments, the hydroprocessing may take place in a reactor at a temperature from 150° C. to 450° C. The temperature in one or more of the hydrotreating unit, hydrocracking unit, and residue hydrocracking unit, for example, may be from 150° C. to 440° C., from 150° C. to 430° C., from 150° C. to 420° C., from 150° C. to 410° C., from 150° C. to 400° C., from 150° C. to 390° C., from 150° C. to 380° C., from 150° C. to 370° C., from 150° C. to 360° C., from 150° C. to 350° C., from 150° C. to 340° C., from 150° C. to 330° C., from 150° C. to 320° C., from 150° C. to 310° C., from 150° C. to 300° C., from 150° C. to 290° C., from 150° C. to 280° C., from 150° C. to 270° C., from 150° C. to 260° C., from 150° C. to 250° C., from 150° C. to 240° C., from 150° C. to 230° C., from 150° C. to 220° C., from 150° C. to 210° C., from 150° C. to 200° C., from 150° C. to 190° C., from 150° C. to 180° C., from 150° C. to 170° C., from 150° C. to 160° C., from 160° C. to 450° C., from 170° C. to 450° C., from 180° C. to 450° C., from 190° C. to 450° C., from 200° C. to 450° C., from 200° C. to 350° C., from 200° C. to 300° C., from 210° C. to 450° C., from 220° C. to 450° C., from 230° C. to 450° C., from 240° C. to 450° C., from 250° C. to 450° C., from 260° C. to 450° C., from 270° C. to 450° C., from 280° C. to 450° C., from 290° C. to 450° C., from 300° C. to 450° C., from 310° C. to 450° C., from 320° C. to 450° C., from 330° C. to 450° C., from 340° C. to 450° C., from 350° C. to 450° C., from 360° C. to 450° C., from 370° C. to 450° C., from 380° C. to 450° C., from 390° C. to 450° C., from 400° C. to 450° C., from 410° C. to 450° C., from 420° C. to 450° C., from 430° C. to 450° C., or even from 440° C. to 450° C. It should be understood that the temperature may be from any lower bound for such temperature disclosed herein to any upper bound for such temperature disclosed herein. Without intending to be bound by any particular theory, it is believed that the necessary reactions will not take place quickly enough to be commercially viable below 150° C., but above 450° C., unwanted byproducts may form and catalyst activity may be greatly diminished due to coke formation.

In embodiments, the hydrogen partial pressure in one or more of the hydrotreating unit, hydrocracking unit, and residue hydrocracking unit, for example, may be from 0.5 MPa to 22 MPa, from 1 MPa to 20 MPa, from 2 MPa to 10 MPa, or from 10 MPa to 20 MPa. It should be understood that the operating pressure may be from any lower bound for such pressure disclosed herein to any upper bound for such pressure disclosed herein. Without intending to be bound by any particular theory, it is believed that the necessary reactions will not take place quickly enough to be commercially viable below 0.5 MPa, but above 22 MPa, the required additional apparatus for withstanding such pressures increase the cost of the capital equipment beyond commercial viability.

In embodiments, the LHSV in one or more of the hydrotreating unit, hydrocracking unit, and residue hydrocracking unit, for example, may be from 0.2 per hour to 10 per hour, from 0.5 per hour to 10 per hour, from 1 per hour to 10 per hour, from 1.5 per hour to 10 per hour, from 2 per hour to 10 per hour, from 2.5 per hour to 10 per hour, from 3 per hour to 10 per hour, from 3.5 per hour to 10 per hour, from 4 per hour to 10 per hour, from 4.5 per hour to 10 per hour, from 5 per hour to 10 per hour, from 5.5 per hour to 10 per hour, from 6 per hour to 10 per hour, from 6.5 per hour to 10 per hour, from 7 per hour to 10 per hour, from 7.5 per hour to 10 per hour, from 8 per hour to 10 per hour, from 8.5 per hour to 10 per hour, from 9 per hour to 10 per hour, from 9.5 per hour to 10 per hour, from 0.2 per hour to 9.5 per hour, from 0.2 per hour to 9 per hour, from 0.2 per hour to 8.5 per hour, from 0.2 per hour to 8 per hour, from 0.2 per hour to 7.5 per hour, from 0.2 per hour to 7 per hour, from 0.2 per hour to 6.5 per hour, from 0.2 per hour to 6 per hour, from 0.2 per hour to 5.5 per hour, from 0.2 per hour to 5 per hour, from 0.2 per hour to 4.5 per hour, from 0.2 per hour to 4 per hour, from 0.2 per hour to 3.5 per hour, from 0.2 per hour to 3 per hour, from 0.2 per hour to 2.5 per hour, from 0.2 per hour to 2 per hour, from 0.2 per hour to 1.5 per hour, from 0.2 per hour to 1 per hour, or even from 0.2 per hour to 0.5 per hour. It should be understood that the LHSV may be from any lower bound for such LHSV disclosed herein to any upper bound for such LHSV disclosed herein.

In embodiments, the amount of hydrocarbon in the hydroprocessor may be at least 1 times the amount of hydrogen consumed, or at least 2 times the hydrogen consumed, or at least 3 times the hydrogen consumed, or even at least 4 times the hydrogen consumed. Without intending to be bound by any particular theory, when there is too little hydrogen, the catalyst may deactivate. However, when there is too much hydrogen, undesired byproducts may form and the cost of supplying the hydrogen may increase.

Hydroprocessing product stream 12, which includes the above-mentioned hydrocarbons and light molecules, may be recovered so that the individual components of the hydroprocessing product stream 12 may be separated from one another. Additionally, sour water stream 14 and $CO_2$ stream 16 may both exit the hydroprocessor 110 for further treatment or disposal.

Figure 2:
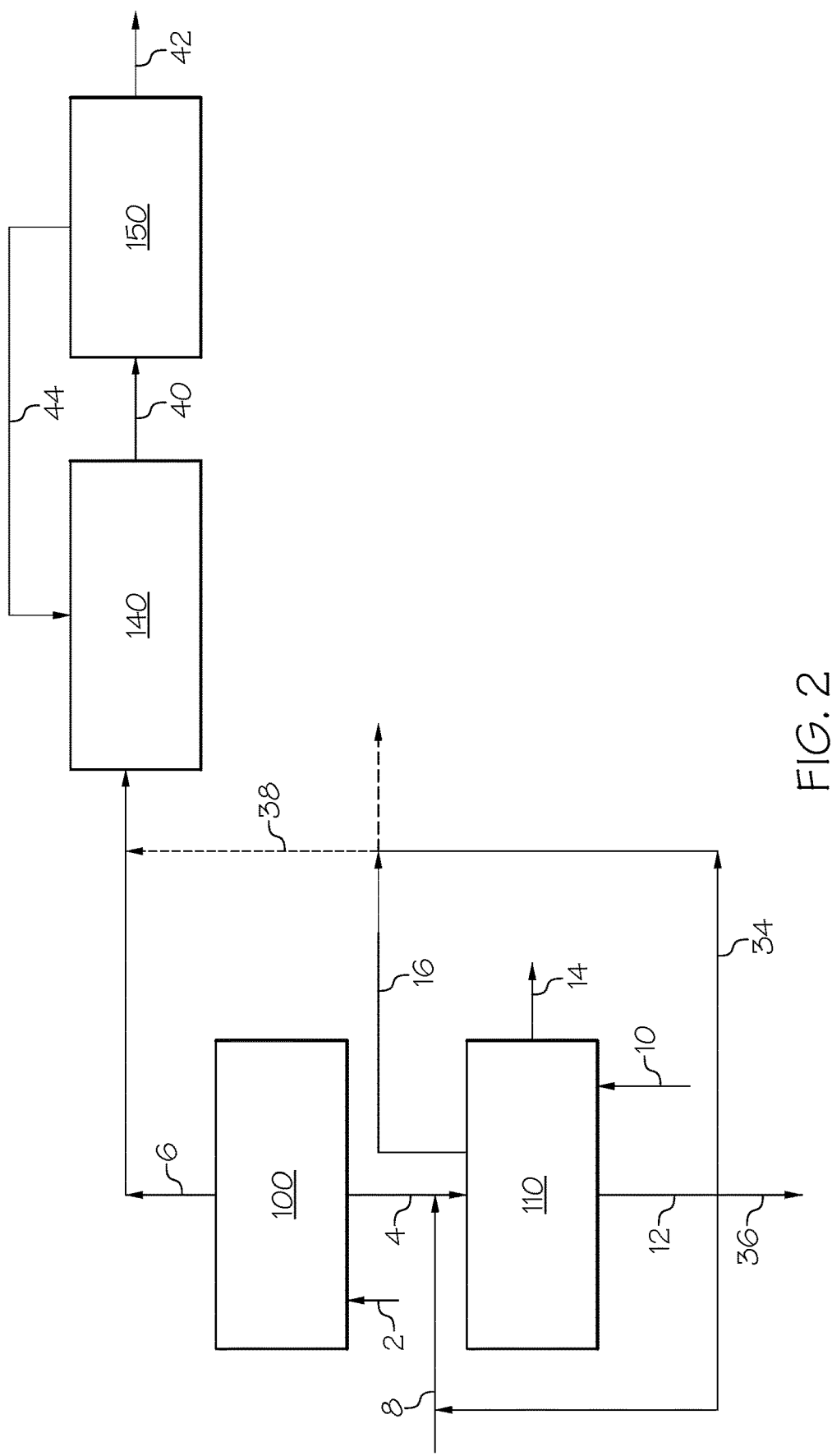
FIG. 2 is a process flow diagram for an exemplary process in accordance with embodiments described herein.

The process of FIG. 1 may be enhanced with additional process steps that allow for further scrubbing of undesirable waste streams. In embodiments, it is possible to hydrogenate $CO_2$ to produce methanol, as shown in FIG. 2. Just as in FIG. 1, hydrogen gas and $CO_2$ are produced in a hydrogen production unit 100. A hydrocarbon feedstock stream 2 is fed to the hydrogen production unit 100. As noted in the context of FIG. 1, the hydrocarbon feedstock may be, for example, natural gas comprising methane as a major constituent, along with ethane, propane, butanes, and hydrocarbons having 5 or more carbon atoms as minor constituents. Within the hydrogen production unit 100, the hydrocarbon feedstock is used to produce hydrogen and $CO_2$, which can be separated into a hydrogen gas feed 4 and a $CO_2$ stream 6 by the same reactions noted above regarding FIG. 1. In embodiments, the hydrogen production unit 100 may include at least one furnace and the $CO_2$ stream 6 may be produced at the at least one furnace. In embodiments, the $CO_2$ stream 6 may be produced as a byproduct of combustion of a natural gas stream with a gas comprising oxygen, such as air, in the at least one furnace.

The resulting hydrogen gas feed 4 may be fed to the hydroprocessor 110 along with the hydroprocessing feedstock stream 8. The hydroprocessing feedstock stream 8 may include one or more of crude oil or its fractions, such as naphtha, kerosene, diesel, vacuum gas oil, or vacuum residue, for example. The hydroprocessing feedstock stream 8 may include hydrocarbons (including, but not limited to, refined oil obtained from crude oil, synthetic crude oil, bitumen, oil sand, shale oil or coal oil, vacuum gas oil (VGO), deasphalted oil (DAO) obtained from a solvent deasphalting process, demetallized oil, light coker gas oil or heavy coker gas oil obtained from a coker process, cycle oil obtained from a fluid catalytic cracking (FCC) process, and gas oil obtained from a visbraking process) and heavy molecules. In addition, water stream 10 may be added to the hydroprocessor 110. Within the hydroprocessor 110, the hydrocarbons of the hydroprocessing feedstock stream 8 may be refined, and the heavy molecules may be cracked into light molecules of high economic value. Such light molecules include, but are not limited to, light gases, C1-C4, light naphtha (C5-C6 boiling in the range 20° C. to 80° C.), heavy naphtha (boiling in the range 80° C. to 180° C.), kerosene (boiling in the range 180° C. to 240° C.), and diesel (boiling in the range 240° C. to 370° C.). Many of these products may be included as components of high value transportation fuels.

Hydroprocessing product stream 12, which includes the above-mentioned hydrocarbons and light molecules, may be recovered and separated into a gas stream 34, which includes recycle hydrogen, and liquid stream 36. Additionally, sour water stream 14 and $CO_2$ stream 16 may both exit the hydroprocessor 110 for further treatment or disposal, as described above.

In embodiments, the $CO_2$ stream 16 may be added to the gas stream 34, and the resulting mixed stream 38 may be sent to the $CO_2$ hydrogenation unit 140. In embodiments, $CO_2$ stream 16 may be bled from the hydroprocessor 110 and not added to the gas stream 34.

The gas stream 34 may be combined with the $CO_2$ stream 6, and both may be sent to the $CO_2$ hydrogenation unit 140. In the $CO_2$ hydrogenation unit 140, the $CO_2$ is hydrogenated to produce hydrogenation effluent 40, which includes methanol and unreacted gases ($CO_2$ and $H_2$, for example). The methanol and unreacted gases may be separated from one another using separator 150, to produce methanol stream 42 and unreacted gas stream 44, which may be recycled back to the $CO_2$ hydrogenation unit '40. In embodiments, the $CO_2$ hydrogenation unit 140 includes at least a fixed bed reactor.

Hydrogenation of $CO_2$ proceeds in accordance with formula (3).

$$CO_2 + H_2\text{(in excess)} \leftrightharpoons CH_3OH \tag{3}$$

In formula (3), hydrogen is included as a reagent in excess. When hydrogen is included in stoichiometric amounts, instead of methanol ($CH_3OH$), the major products are carbon monoxide and water. The hydrogenation of $CO_2$ takes place in the presence of a catalyst. In embodiments, the hydrogenation catalyst may include an active-phase metal on a support. In embodiments, the active-phase metal may be selected from the group consisting of nickel, molybdenum, tungsten, platinum, palladium, rhodium, ruthenium, gold, and a combination of two or more of these. In embodiments, the support may be selected from the group consisting of amorphous alumina, crystalline silica-alumina, alumina, silica, and a combination of two or more thereof.

In embodiments, the hydrogen used in the hydrogenation of the $CO_2$ may be from any source within a refinery. For instance, hydrogen may be generated in one or more of: (1) a steam-methane reformer (SMR); (2) a catalytic reformer (CR); and (3) a gasification unit. The SMR uses methane as a feedstock and provides high purity hydrogen. For instance, the SMR product stream may be greater than 95 volume % (vol %) hydrogen, or greater than 97 vol % hydrogen, or greater than 99 vol % hydrogen, or even greater than 99.5 vol % hydrogen. The CR uses heavy naphtha containing primarily $C_7$ to $C_{12}$ hydrocarbons and provides relatively lower purity hydrogen. For instance, the CR product stream may contain from 85 vol % to 90 vol % hydrogen. The gasification unit uses a carbonaceous material to produce syngas (CO and $H_2$).

In embodiments, the hydrogen used in the hydrogenation of the $CO_2$ may be produced as a low-pressure hydrogen stream from a hydroprocessor, where "low-pressure" refers to a pressure from 2 Mpa to 6 Mpa in this context. In embodiments, the hydroprocessor from which the low-pressure hydrogen stream is produced may be hydroprocessor 110. Traditionally, this low-pressure hydrogen stream could not be recovered cost effectively and was treated as a waste stream. However, using this waste stream for the hydrogenation of $CO_2$ allows the hydrogenation to be conducted with hydrogen that would otherwise represent a cost of the process. As a result, the hydrogenation of $CO_2$ becomes more economically feasible. In many refineries, the hydrogen stream is valuable and may be recovered. However, in some refineries, the hydrogen stream is flared because the separation is not economically feasible. As a result, when $CO_2$ was hydrogenated traditionally, "make-up" hydrogen was added to such refining systems. The presently described subject matter minimizes the need for the use of make-up hydrogen.

In embodiments, hydrogenation of the $CO_2$ may take place in a reactor at a temperature from 150° C. to 400° C. The temperature for hydrogenation of $CO_2$ may be, for example, from 150° C. to 390° C., from 150° C. to 380° C., from 150° C. to 370° C., from 150° C. to 360° C., from 150° C. to 350° C., from 150° C. to 340° C., from 150° C. to 330° C., from 150° C. to 320° C., from 150° C. to 310° C., from 150° C. to 300° C., from 150° C. to 290° C., from 150° C. to 280° C., from 150° C. to 270° C., from 150° C. to 260° C., from 150° C. to 250° C., from 150° C. to 240° C., from 150° C. to 230° C., from 150° C. to 220° C., from 150° C. to 210° C., from 150° C. to 200° C., from 150° C. to 190° C., from 150° C. to 180° C., from 150° C. to 170° C., from 150° C. to 160° C., from 160° C. to 400° C., from 170° C. to 400° C., from 180° C. to 400° C., from 190° C. to 400° C., from 200° C. to 400° C., from 200° C. to 350° C., from 200° C. to 300° C., from 210° C. to 400° C., from 220° C. to 400° C., from 230° C. to 400° C., from 240° C. to 400° C., from 250° C. to 400° C., from 260° C. to 400° C., from 270° C. to 400° C., from 280° C. to 400° C., from 290° C. to 400° C., from 300° C. to 400° C., from 310° C. to 400° C., from 320° C. to 400° C., from 330° C. to 400° C., from 340° C. to 400° C., from 350° C. to 400° C., from 360° C. to 400° C., from 370° C. to 400° C., from 380° C. to 400° C., or even from 390° C. to 400° C. It should be understood that the temperature may be from any lower bound for such temperature disclosed herein to any upper bound for such temperature disclosed herein. Without being bound by theory, methanol selectivity may be negatively impacted at temperatures below the lower bound and temperatures may undesirably impact reactivity.

In embodiments, hydrogenation of the $CO_2$ may take place at a total pressure from 0.2 MPa to 6 MPa, from 0.2 MPa to 5.8 MPa, from 0.2 MPa to 5.6 MPa, from 0.2 MPa to 5.4 MPa, from 0.2 MPa to 5.2 MPa, from 0.2 MPa to 5 MPa, from 0.2 MPa to 4.8 MPa, from 0.2 MPa to 4.6 MPa, from 0.2 MPa to 4.4 MPa, from 0.2 MPa to 4.2 MPa, from 0.2 MPa to 4 MPa, from 0.2 MPa to 3.8 MPa, from 0.2 MPa to 3.6 MPa, from 0.2 MPa to 3.4 MPa, from 0.2 MPa to 3.2 MPa, from 0.2 MPa to 3 MPa, from 0.2 MPa to 2.8 MPa, from 0.2 MPa to 2.6 MPa, from 0.2 MPa to 2.4 MPa, from 0.2 MPa to 2.2 MPa, from 0.2 MPa to 2 MPa, from 0.2 MPa to 1.8 MPa, from 0.2 MPa to 1.6 MPa, from 0.2 MPa to 1.4 MPa, from 0.2 MPa to 1.2 MPa, from 0.2 MPa to 1 MPa, from 0.2 MPa to 0.8 MPa, from 0.2 MPa to 0.6 MPa, from 0.2 MPa to 0.4 MPa, from 0.4 MPa to 6 MPa, from 0.6 MPa to 6 MPa, from 0.8 MPa to 6 MPa, from 1 MPa to 6 MPa, from 1 MPa to 4 MPa, from 1.2 MPa to 6 MPa, from 1.4 MPa to 6 MPa, from 1.6 MPa to 6 MPa, from 1.8 MPa to 6 MPa, from 2 MPa to 6 MPa, from 2 MPa to 3 MPa, from 2.2 MPa to 6 MPa, from 2.4 MPa to 6 MPa, from 2.6 MPa to 6 MPa, from 2.8 MPa to 6 MPa, from 3 MPa to 6 MPa, from 3.2 MPa to 6 MPa, from 3.4 MPa to 6 MPa, from 3.6 MPa to 6 MPa, from 3.8 MPa to 6 MPa, from 4 MPa to 6 MPa, from 4.2 MPa to 6 MPa, from 4.4 MPa to 6 MPa, from 4.6 MPa to 6 MPa, from 4.8 MPa to 6 MPa, from 5 MPa to 6 MPa, from 5.2 MPa to 6 MPa, from 5.4 MPa to 6 MPa, from 5.6 MPa to 6 MPa, or even from 5.8 MPa to 6 MPa. It should be understood that the operating pressure may be from any lower bound for such pressure disclosed herein to any upper bound for such pressure disclosed herein. Without being bound by theory, partial pressures below the lower bound may decrease conversion.

In embodiments, the reactor used for hydrogenation of the $CO_2$ may be operated at a GHSV from 5000 liters per kilogram of catalyst per hour (l/kg/h) to 30000 l/kg/h, from 6000 l/kg/h to 30000 l/kg/h, from 7000 l/kg/h to 30000 l/kg/h, from 7000 l/kg/h to 25000 l/kg/h, from 8000 l/kg/h to 30000 l/kg/h, from 9000 l/kg/h to 30000 l/kg/h, from 10000 l/kg/h to 30000 l/kg/h, from 10000 l/kg/h to 20000 l/kg/h, from 11000 l/kg/h to 30000 l/kg/h, from 12000 l/kg/h to 30000 l/kg/h, from 13000 l/kg/h to 30000 l/kg/h, from 14000 l/kg/h to 30000 l/kg/h, from 15000 l/kg/h to 30000 l/kg/h, from 16000 l/kg/h to 30000 l/kg/h, from 17000 l/kg/h to 30000 l/kg/h, from 18000 l/kg/h to 30000 l/kg/h, from 19000 l/kg/h to 30000 l/kg/h, from 20000 l/kg/h to 30000 l/kg/h, from 21000 l/kg/h to 30000 l/kg/h, from 22000 l/kg/h to 30000 l/kg/h, from 23000 l/kg/h to 30000 l/kg/h, from 24000 l/kg/h to 30000 l/kg/h, from 25000 l/kg/h to 30000 l/kg/h, from 26000 l/kg/h to 30000 l/kg/h, from 27000 l/kg/h to 30000 l/kg/h, from 28000 l/kg/h to 30000 l/kg/h, from 29000 l/kg/h to 30000 l/kg/h, from 5000 l/kg/h to 29000 l/kg/h, from 5000 l/kg/h to 28000 l/kg/h, from 5000 l/kg/h to 27000 l/kg/h, from 5000 l/kg/h to 26000 l/kg/h, from 5000 l/kg/h to 25000 l/kg/h, from 5000 l/kg/h to 24000 l/kg/h, from 5000 l/kg/h to 23000 l/kg/h, from 5000 l/kg/h to 22000 l/kg/h, from 5000 l/kg/h to 21000 l/kg/h, from 5000 l/kg/h to 20000 l/kg/h, from 5000 l/kg/h to 19000 l/kg/h, from 5000 l/kg/h to 18000 l/kg/h, from 5000 l/kg/h to 17000 l/kg/h, from 5000 l/kg/h to 16000 l/kg/h, from 5000 l/kg/h to 15000 l/kg/h, from 5000 l/kg/h to 14000 l/kg/h, from 5000 l/kg/h to 13000 l/kg/h, from 5000 l/kg/h to 12000 l/kg/h, from 5000 l/kg/h to 11000 l/kg/h, from 5000 l/kg/h to 10000 l/kg/h, from 5000 l/kg/h to 9000 l/kg/h, from 5000 l/kg/h to 8000 l/kg/h, from 5000 l/kg/h to 7000 l/kg/h, or even from 5000 l/kg/h to 6000 l/kg/h. It should be understood that the GHSV may be from any lower bound for such GHSV disclosed herein to any upper bound for such GHSV disclosed herein.

In embodiments, the reactor used for hydrogenation of the $CO_2$ may be operated at a hydrogen-to-$CO_2$ ratio from 2 mol/mol to 10 mol/mol, from 2 mol/mol to 9.5 mol/mol, from 2 mol/mol to 9 mol/mol, from 2 mol/mol to 8.5 mol/mol, from 2 mol/mol to 8 mol/mol, from 2 mol/mol to 7.5 mol/mol, from 2 mol/mol to 7 mol/mol, from 2 mol/mol to 6.5 mol/mol, from 2 mol/mol to 6 mol/mol, from 2 mol/mol to 5.5 mol/mol, from 2 mol/mol to 5 mol/mol, from 2 mol/mol to 4.5 mol/mol, from 2 mol/mol to 4 mol/mol, from 2 mol/mol to 3.5 mol/mol, from 2 mol/mol to 3 mol/mol, from 2 mol/mol to 2.5 mol/mol, from 2.5 mol/mol to 10 mol/mol, from 3 mol/mol to 10 mol/mol, from 3.5 mol/mol to 10 mol/mol, from 4 mol/mol to 10 mol/mol, from 4.5 mol/mol to 10 mol/mol, from 5 mol/mol to 10 mol/mol, from 5.5 mol/mol to 10 mol/mol, from 6 mol/mol to 10 mol/mol, from 6.5 mol/mol to 10 mol/mol, from 7 mol/mol to 10 mol/mol, from 7.5 mol/mol to 10 mol/mol, from 8 mol/mol to 10 mol/mol, from 8.5 mol/mol to 10 mol/mol, from 9 mol/mol to 10 mol/mol, or even from 9.5 mol/mol to 10 mol/mol. It should be understood that the hydrogen-to-$CO_2$ ratio may be from any lower bound for such hydrogen-to-$CO_2$ ratio disclosed herein to any upper bound for such hydrogen-to-$CO_2$ ratio disclosed herein. Without being bound by theory, at levels below the hydrogen-to-$CO_2$ lower bound, there may be insufficient hydrogen for the $CO_2$ conversion.

According to an aspect, either alone or in combination with any other aspect, a process for producing methanol and hydrocarbon products comprises: generating hydrogen gas and carbon dioxide in a hydrogen production unit; hydroprocessing a hydrocarbon feedstock stream using the hydrogen gas, thereby producing hydrocarbon products and waste hydrogen gas; and contacting the waste hydrogen gas with the carbon dioxide in a hydrogenation unit, thereby producing methanol and product hydrogen gas.

According to a second aspect, either alone or in combination with any other aspect, the process for producing methanol and hydrocarbon products may comprise generating the hydrogen gas and carbon dioxide comprises contacting a natural gas stream with steam in the hydrogen production unit.

According to a third aspect, either alone or in combination with any other aspect, the process for producing methanol and hydrocarbon products further discloses that the hydrogen production unit comprises at least one furnace and the carbon dioxide is produced in the at least one furnace.

According to a fourth aspect, either alone or in combination with any other aspect, the process for producing methanol and hydrocarbon products discloses the carbon dioxide is produced as a byproduct of combustion of a natural gas stream with a gas comprising oxygen in the at least one furnace.

According to a fifth aspect, either alone or in combination with any other aspect, the process for producing methanol and hydrocarbon products discloses that the hydrogenation unit is operated at a temperature from 150° C. to 400° C.

According to a sixth aspect, either alone or in combination with any other aspect, the process for producing methanol and hydrocarbon products discloses the hydrogen gas enters the hydrogenation unit at a partial pressure from 3 MPa to 6 MPa.

According to a seventh aspect, either alone or in combination with any other aspect, the process for producing methanol and hydrocarbon products discloses that the hydrogenation unit is a component of a hydroprocessor, which further comprises a reactor unit selected from the group consisting of a hydrotreating unit, a hydrocracking unit, a residue hydrocracking unit, and a combination of two or more thereof.

According to an eighth aspect, either alone or in combination with any other aspect, wherein hydroprocessing the hydrocarbon feedstock takes place in the hydroprocessor.

According to a ninth aspect, either alone or in combination with any other aspect, wherein the hydroprocessor is operated at a temperature from 150° C. to 450° C.

According to a tenth aspect, either alone or in combination with any other aspect, wherein the hydroprocessor is operated at a pressure from 1 MPa to 25 MPa.

According to an eleventh aspect, either alone or in combination with any other aspect, wherein the hydrocarbon feedstock is selected from the group consisting of a whole crude oil stream, a naphtha stream, a distillate stream, a vacuum gas oil stream, a residue stream, an intermediate refinery stream, and a combination of two or more thereof.

According to a twelfth aspect, either alone or in combination with any other aspect, wherein the hydrogen gas supplied by a recycle gas stream of the hydroprocessor.

According to a thirteenth aspect, either alone or in combination with any other aspect, an integrated system for producing methanol and hydrocarbon products using hydrogen gas and carbon dioxide comprises: at least one source of the hydrogen gas; at least one source of the carbon dioxide; and at least one hydrogenation unit in fluid communication with the at least one source of the carbon dioxide and the at least one source of the hydrogen gas.

According to a fourteenth aspect, either alone or in combination with any other aspect, an integrated system for producing methanol and hydrocarbon products may include a hydrogen production unit is the at least one source of the carbon dioxide and the at least one source of the hydrogen gas.

According to a fifteenth aspect, either alone or in combination with any other aspect, an integrated system for producing methanol and hydrocarbon products may include at least one hydrogenation unit is a component of a hydroprocessor, the hydroprocessor further comprising a reactor unit selected from the group consisting of a hydrotreating unit, a hydrocracking unit, a residue hydrocracking unit, and a combination of two or more thereof.

According to a sixteenth aspect, either alone or in combination with any other aspect, an integrated system for producing methanol and hydrocarbon products may disclose that the hydrogen production unit comprises at least one furnace and the at least one furnace is the at least one source of carbon dioxide.

According to a seventeenth aspect, either alone or in combination with any other aspect, wherein the source of the hydrogen gas is supplied by a recycle gas stream of the hydrogenation unit.

EXAMPLE

Using embodiments described above, an exemplary integrated hydroprocessing and hydrogenation system and process may be performed as follows. The following example is merely illustrative and should not be interpreted as limiting the scope of the present disclosure.

In a pilot scale process, 4400 kg of $CO_2$ mixture obtained from hydrogen production and hydrotreating units is combined with 806 kg of the recycle hydrogen originating from hydrotreating unit and then sent to a $CO_2$ hydrogenation unit. The hydrogen and $CO_2$ mixture, at a mole ratio of hydrogen to $CO_2$ of 4, is pressurized to 5 MPa (hydrogen partial pressure of 4 MPa and $CO_2$ partial pressure of 1 Mpa) and heated to 300° C. This pressurized stream is sent to the $CO_2$ hydrogenation reactor containing Indium-Cobalt catalyst and processed at a weighted hourly space velocity of 2 $h^{-1}$ or gas liquid hourly space velocity of 15000 $h^{-1}$. 546 kg of methanol is produced in the process and 4,475 kg of unreacted hydrogen and $CO_2$ gas mixture is recycled back to the reactor.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used in this disclosure and in the appended claims, the words "comprise," "has," and "include" and all grammatical variations thereof are each intended to have an open, non-limiting meaning that does not exclude additional elements or steps.

As used in this disclosure, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. A process for producing methanol and hydrocarbon products, the process comprising:
    feeding a hydrocarbon feedstock stream comprising methane as a major constituent to a hydrogen production unit comprising at least one furnace;
    generating hydrogen gas and carbon dioxide in the hydrogen production unit, wherein the hydrogen production unit is operated at a temperature from 700° C. to 1000° C. and a pressure from 0.3 MPa to 2.5 MPa;
    feeding the generated hydrogen gas, a hydroprocessing feedstock stream, and water to a hydrocracking unit;
    hydrocracking the hydroprocessing feedstock stream in the hydrocracking unit using the generated hydrogen gas, thereby producing hydrocarbon products, waste carbon dioxide, and waste hydrogen gas,
    wherein an amount of the hydroprocessing feedstock stream in the hydrocracking unit is added in excess of the generated hydrogen consumed during the hydrocracking;
    feeding the generated carbon dioxide and a mixed gas stream comprising the waste carbon dioxide and waste hydrogen from the hydrocracking unit to a hydrogenation unit; and
    contacting the waste hydrogen gas with the generated carbon dioxide and the waste carbon dioxide in the hydrogenation unit, thereby producing methanol and product hydrogen gas,
    wherein the hydrogenation unit is operated at a hydrogen to carbon dioxide ratio from 2 mol/mol to 10 mol/mol.

2. The process of claim 1, wherein generating the hydrogen gas and carbon dioxide comprises contacting a natural gas stream with steam in the hydrogen production unit.

3. The process of claim 1, wherein the carbon dioxide is produced as a byproduct of combustion of a natural gas stream with a gas comprising oxygen in the at least one furnace.

4. The process of claim 1, wherein the hydrogenation unit is operated at a temperature from 150° C. to 400° C.

5. The process of claim 1, wherein the hydrogen gas enters the hydrogenation unit at a partial pressure from 3 MPa to 6 MPa.

6. The process of claim 1, wherein the hydrogenation unit is a component of a hydroprocessor, which further comprises a reactor unit selected from the group consisting of a hydrotreating unit, a hydrocracking unit, a residue hydrocracking unit, and a combination of two or more thereof.

7. The process of claim 1, wherein the hydrocracking unit is operated at a temperature from 150° C. to 450° C.

8. The process of claim 1, wherein the hydrocracking unit is operated at a pressure from 1 MPa to 25 MPa.

9. The process of claim 1, wherein the hydrocarbon feedstock stream is selected from the group consisting of a whole crude oil stream, a naphtha stream, a distillate stream, a vacuum gas oil stream, a residue stream, an intermediate refinery stream, and a combination of two or more thereof.

10. The process of claim 1, wherein the hydrogen gas is supplied by a recycle gas stream of the hydrocracking unit.

* * * * *